(12) United States Patent
Ying

(10) Patent No.: US 10,624,433 B2
(45) Date of Patent: Apr. 21, 2020

(54) MULTIFUNCTIONAL INTELLIGENT SUITCASE

(71) Applicant: HANGZHOU CHIC INTELLIGENT TECHNOLOGY CO., LTD, Hangzhou, Zhejiang (CN)

(72) Inventor: Jiawei Ying, Zhejiang (CN)

(73) Assignee: HANGZHOU CHIC INTELLIGENT TECHNOLOGY CO., LTD., Hangzhou, Zhejiang (CN)

(*) Notice: Subject to any disclaimer, the term of this patent is extended or adjusted under 35 U.S.C. 154(b) by 0 days.

(21) Appl. No.: 16/306,579

(22) PCT Filed: Aug. 12, 2016

(86) PCT No.: PCT/CN2016/095035
§ 371 (c)(1),
(2) Date: Dec. 2, 2018

(87) PCT Pub. No.: WO2017/206353
PCT Pub. Date: Dec. 7, 2017

(65) Prior Publication Data
US 2019/0142126 A1 May 16, 2019

(30) Foreign Application Priority Data

Jun. 3, 2016 (CN) .......................... 2016 1 0389640
Aug. 3, 2016 (CN) .......................... 2016 1 0634198

(51) Int. Cl.
*A45C 13/18* (2006.01)
*A45C 5/14* (2006.01)
(Continued)

(52) U.S. Cl.
CPC ............... *A45C 13/18* (2013.01); *A45C 5/03* (2013.01); *A45C 5/14* (2013.01); *G01G 19/021* (2013.01);
(Continued)

(58) Field of Classification Search
None
See application file for complete search history.

(56) References Cited

U.S. PATENT DOCUMENTS

| 10,023,151 | B2* | 7/2018 | Samadani .......... G07C 9/00174 |
| 2014/0107868 | A1 | 4/2014 | DiGiacomcantonio et al. |
| 2019/0373998 | A1* | 12/2019 | Knittel ...................... A45F 3/04 |

FOREIGN PATENT DOCUMENTS

| CN | 103251194 | 8/2013 |
| CN | 204132628 | 2/2015 |

(Continued)

OTHER PUBLICATIONS

"International Search Report (Form PCT/ISA/210)", dated Jan. 25, 2017, with English translation thereof, pp. 1-6.

*Primary Examiner* — Carlos Garcia
(74) *Attorney, Agent, or Firm* — JCIPRNET

(57) ABSTRACT

The present invention discloses a multifunctional intelligent suitcase comprising a suitcase body and a mobile control terminal. The suitcase body is provided with an electronic combination lock, a microprocessor, an electronic switch, a power supply module, an LED strip and an air quality monitoring module. The control ends of the electronic combination lock and the electronic switch and the air quality monitoring module are connected to the microprocessor. The input end and output end of the electronic switch are respectively connected to the power supply module and LED strip. The air quality monitoring module is used to collect current air quality information and send the information to the microprocessor. The microprocessor determines current air quality information, and when it does not meet the healthy air quality index, will control the electronic switch to turn on. The mobile control terminal comprises a controller and a touch LCD screen. The controller is wirelessly connected to the microprocessor. The touch LCD (Continued)

screen is used for consumers to input operation information. The controller, according to input operating information, controls the microprocessor to take corresponding action.

10 Claims, 7 Drawing Sheets

(51) Int. Cl.
  *A45C 5/03* (2006.01)
  *G01G 19/02* (2006.01)
  *G01N 33/00* (2006.01)
  *G07C 9/00* (2020.01)
  *A45C 13/00* (2006.01)

(52) U.S. Cl.
  CPC ..... *G01N 33/0063* (2013.01); *G01N 33/0073* (2013.01); *G07C 9/0069* (2013.01); *G07C 9/00309* (2013.01); *G07C 9/00896* (2013.01); *A45C 13/00* (2013.01); *A45C 2005/037* (2013.01); *G07C 2009/0092* (2013.01)

(56) References Cited

FOREIGN PATENT DOCUMENTS

| | | |
|---|---|---|
| CN | 204467229 | 7/2015 |
| CN | 104824944 | 8/2015 |
| CN | 204920522 | 12/2015 |
| CN | 105919257 | 9/2016 |

\* cited by examiner

MULTIFUNCTIONAL INTELLIGENT SUITCASE

CROSS-REFERENCE TO RELATED APPLICATION

This application is a 371 application of an international PCT application serial no. PCT/CN2016/095035, filed on Aug. 12, 2016, which claims priority to and the benefit of China Patent Application No. CN201610389640.5, filed on Jun. 3, 2016, and of China Patent Application No. CN201610634198.8, filed on Aug. 3, 2016. The entirety of each of the above-mentioned patent applications is hereby incorporated by reference herein and made a part of this specification.

FIELD OF THE INVENTION

The present invention relates to a suitcase technology, and more specially relates to a multifunctional intelligent suitcase.

DESCRIPTION OF THE PRIOR ART

In travel, all kinds of suitcase are tourists' first choice and even treasures are placed in the suitcases. The present suitcases are mostly provided with coded lock to protect the articles in the suitcase from stealing, offering only a single function.

SUMMARY OF THE INVENTION

It is the object of the present invention to provide a multifunctional intelligent suitcase to solve the problem of only a single function for a suitcase.

The embodiment of the present invention provides a multifunctional intelligent suitcase comprising a suitcase body and a mobile control terminal. Said suitcase body is provided with an electronic combination lock, a microprocessor, a first Bluetooth communication module, a first remote wireless communication module, an electronic switch, a power supply module, an LED strip and an air quality monitoring module. Said electronic combination lock, said first Bluetooth communication module and said remote wireless communication module are all connected to said microprocessor. Said mobile control terminal comprises a controller, a second Bluetooth communication module, a second remote wireless communication module and a touch LCD screen. Said second Bluetooth communication module, said second remote wireless communication module and said touch LCD screen are all connected to said controller. Said second Bluetooth communication module is one-to-one wirelessly connected with said first Bluetooth communication module. Said first remote wireless communication module is one-to-one wirelessly connected with said second remote wireless communication module. In the connection between said first Bluetooth communication module and said second Bluetooth communication module, said microprocessor and said controller realize mutual data transmission via Bluetooth communication. Said touch LCD screen is used for consumers to input operation information. Said operation information comprises unlocking setting instruction, set unlocking password, unlocking instruction and unlocking password. Said controller is used to control said microprocessor to set unlock said electronic combination lock in accordance with said operation information. The input end, control end and output end of said electronic switch are respectively connected to said power supply module, said microprocessor and said LED strip. Said air quality monitoring module is connected to said microprocessor to collect the information of current air quality and transmit the information collected to said microprocessor. Said microprocessor stores the data of healthy air for comparison and judgment. When it determines that the current air quality fails to meet the data of healthy air, said microprocessor will output a signal to switch-on said electronic switch and enable said LED strip to light up.

Further, said controller comprises password setting module and a control module connected to said password setting module. Said microprocessor comprises a processing module and a storing module connected to said processing module. Said password setting module is used to generate said unlocking password setting instruction and given unlocking password. Said control module receives said unlocking password setting instruction and given unlocking password, and controls said processing module to store said given unlocking password in said storing module.

Furthermore, said controller also comprises the unlocking module connected to said control module. Said unlocking module is used to generate said unlocking instruction and said unlocking password. Said control module receives said unlocking instruction and said unlocking password, and transmits said unlocking instruction and said unlocking password to said processing module. Said processing module determines whether said unlocking password matches the given unlocking password stored in said storing module, and when both match each other; said processing module unlocks the electronic combination lock.

Furthermore, said mobile control terminal still comprises a voice collector that is connected to said controller. Said touch LCD screen is used for consumers to input audio acquisition instruction to said controller. Said controller, after receiving said audio acquisition instruction, starts said voice collector. Said voice collector is used to collect consumers' audio signals and transmit said audio signals to said controller. Said controller then transmits said audio signals to said microprocessor.

Furthermore, said multifunctional intelligent suitcase comprises a battery compartment that consists of a one-side-openable compartment body, a clamshell and a slide-snap module. Said compartment body is used to accept the batteries of power supply module and mount onto the upper case body of said suitcase. One end of said clamshell is hinged to said compartment body, and the other end of said clamshell is provided with said securing module. When said clamshell is recovered to said compartment body, said slide-snap module is coupled to the buckle of said compartment body.

Furthermore, said slide-snap module comprises slide cavity, slide snap and at least an elastic element. Said slide cavity is detachably mounted onto said clamshell. Said slide snap locates inside said slide cavity and slides along the slide cavity. Said slide snap is provided with a tab on its top. Said compartment body is correspondently provided with a buckle hole on its top to match said tab. Said elastic element is provided between the bottom of said slide snap and said slide cavity. When said clamshell is pushed to cover said compartment body, the reversion strength of said elastic element promotes said slide snap to move in the direction of said buckle hole.

Furthermore, said clamshell is provided with an operation mouth across both faces of the clamshell. Said slide-snap module is disposed behind said clamshell, and said operation mouth is arranged opposite said slide snap.

Furthermore, said suitcase body is provided with roller wheels in its bottom. Said suitcase is also arranged inside its body with a hub motor to drive said roller wheels and radio-frequency signal transmitter. Both said hub motor and said radio-frequency signal transmitter are connected to said microprocessor. Said mobile control terminal also comprises radio-frequency signal feedback device that can wireless connect said radio-frequency signal transmitter, so that the actual distance between the transmitter and the feedback device can be calculated. Said microprocessor stores a given following distance. Said microprocessor receives said actual distance to determine whether said actual distance is farther than said following distance, and when said actual distance is farther than said following distance, said microprocessor will start said hub motor.

Furthermore, said radio-frequency signal transmitter comprises a first transmitter-receiver module and a distance calculation module connected to said first transmitter-receiver module.

Said first transmitter-receiver module is used to send electromagnetic wave signals to said radio-frequency signal feedback device and receive the feedback signals from said radio-frequency signal feedback device; said distance calculation module is used to, according to the feedback signals, calculate the actual distance between said radio-frequency signal transmitter and said radio-frequency signal feedback device, and send the actual distance to said microprocessor.

Furthermore, said radio-frequency signal feedback device comprises a second transmitter-receiver module and a feedback signal generation module connected to said second transmitter-receiver module. Said second transmitter-receiver module is used to receive the electromagnetic wave signals sent from said radio-frequency signal transmitter and send the feedback signals to said radio-frequency signal transmitter; said feedback signal generation module is used to generate feedback signals.

Compared to the prior art, the multifunctional intelligent suitcase of the present invention has the facilitating functions of remote unlocking, remote password setting, air quality monitor, battery loading and unloading, and automatic tracing.

The following embodiments are to further describe the present invention in combination with the above accompanying drawings.

DETAILED DESCRIPTION OF THE PREFERRED EMBODIMENTS

Figure 1:
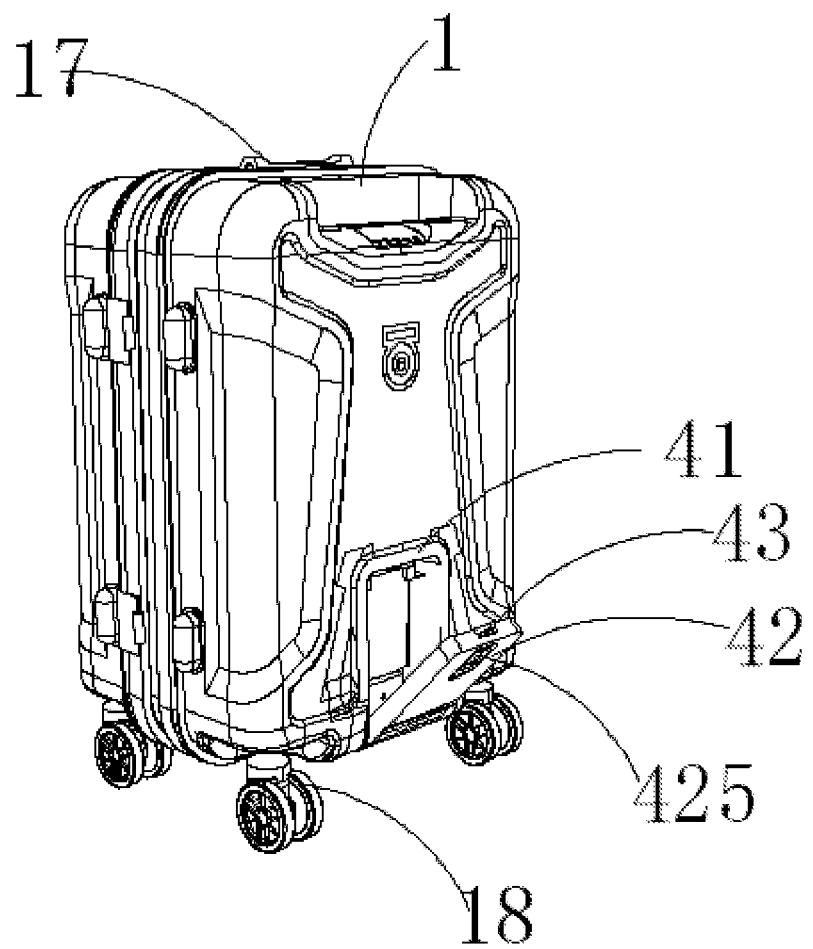
FIG. 1 is a schematic view of multifunctional intelligent suitcase of the present invention.
Figure 2:
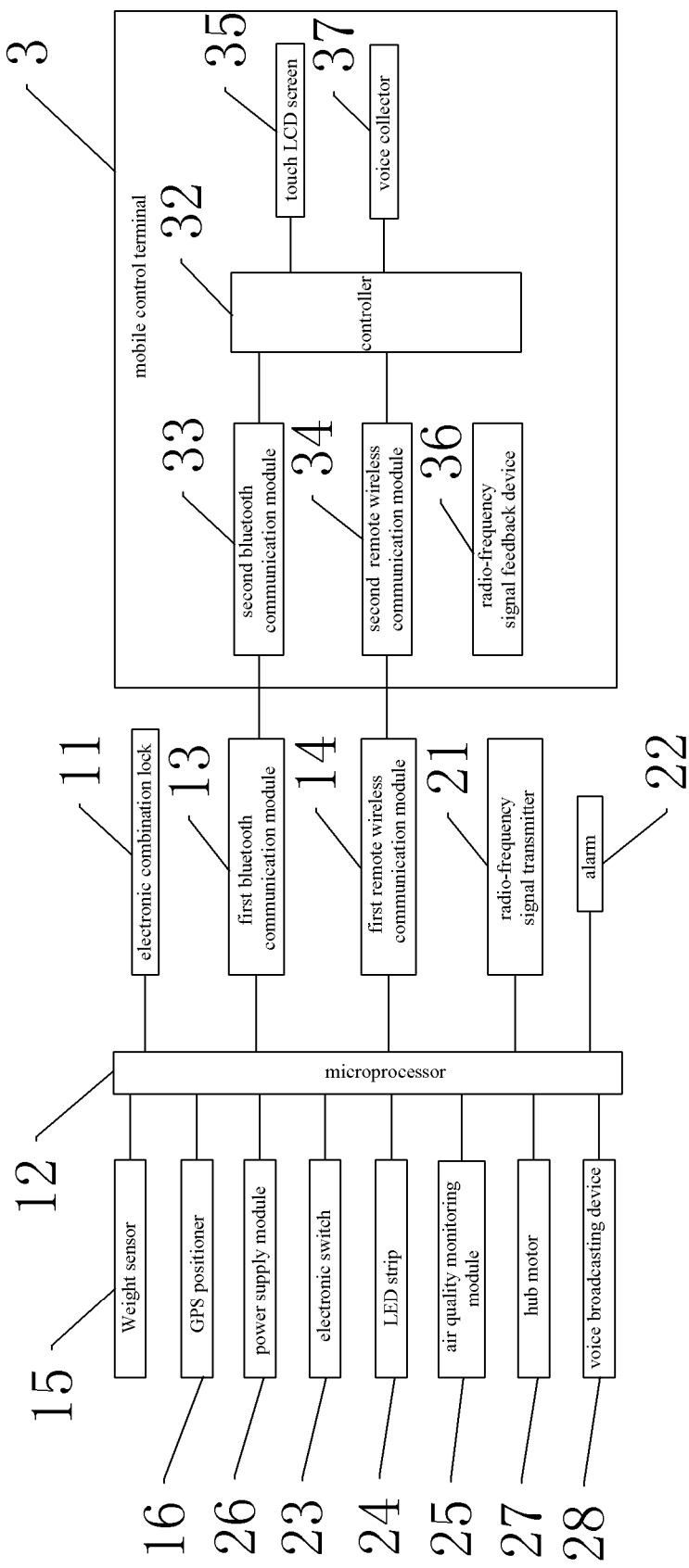
FIG. 2 is a functional block diagram of multifunctional intelligent suitcase of the present invention.

Reference will now be made in greater detail to exemplary embodiments of the invention offering with reference to the accompanying drawings:

See FIG. 1 and FIG. 2. The embodiment of the present invention provides a multi-function intelligent suitcase that comprises suitcase body 1 and mobile control terminal 3.

The suitcase body 1 is provided with an electronic combination lock 11, a microprocessor 12, a first Bluetooth communication module 13, a first remote wireless communication module 14, a weight sensor 15 and a handle (not shown in the drawing) connected to the weight sensor 15. The electronic combination lock 11, first Bluetooth communication module 13, remote wireless communication module 14 and weight sensor 15 are all connected to the microprocessor 12.

The mobile control terminal 3 may optionally be a personal mobile phone that comprises a controller 32, a second Bluetooth communication module 33, a second remote wireless communication module 34 and a touch LCD screen 35. The second Bluetooth communication module 33, the second remote wireless communication module 34 and the touch LCD screen 35 are all connected to the controller 32. The second Bluetooth communication module 33 is one-to-one wirelessly connected with the first Bluetooth communication module 13, and the first remote wireless communication module 14 is one-to-one wirelessly connected with the second remote wireless communication module 34.

It is understood that the controller 32 and the microprocessor 12 can be mutually wirelessly connected via both Bluetooth communication modules and both remote wireless communication modules. The suitcase body 1 and mobile control terminal 3 is respectively provided with a network communication alternation module. When both Bluetooth communication modules can be normally connected, the mode of Bluetooth communication is preferably selected for data transmission; when both Bluetooth communication modules cannot be normally connected, both remote wireless communication modules are used for data transmission. It is to be explained that the Bluetooth communication modules are selected for data transmission, and normally for near-range data transmission. The so-called near-range data transmission means the distance between suitcase 1 and mobile control terminal 3 is 0-100 m that is the effective connection distance between two Bluetooth modules. By near-range data transmission, the selection of Bluetooth communication module for data transmission is able to guarantee quicker data transmission between suitcase 1 and mobile control terminal 3, and save network sources at the same time.

The touch LCD screen 35 is used for consumers to input operation information, and then the controller 32 controls the microprocessor 12 to execute corresponding operation in accordance with the operation command input by consumers. In this embodiment, consumers optionally input unlocking password setting instruction and given unlocking password in the touch LCD screen 35, and the controller 32 controls the microprocessor 12 to set the unlocking password of the electronic combination lock 11; Consumers optionally input unlocking instruction and unlocking password in the touch LCD screen 35, and the controller 32 controls the microprocessor 12 to unlock the electronic combination lock 11;

The weight sensor 15 is used to sense the weight information of suitcase body 1, and send the information to the controller 32 through microprocessor 12. The operation information input by consumers also includes weight information acquisition instruction. When consumers input weight information acquisition instruction through the touch LCD screen 35, the controller 32 displays the weight information on the touch LCD screen 35 to facilitate consumers to know the weight of the suitcase body 1. Specifically, consumers enable the weight sensor 15 to sense the weight of suitcase body 1 through operating the handle.

Figure 3:
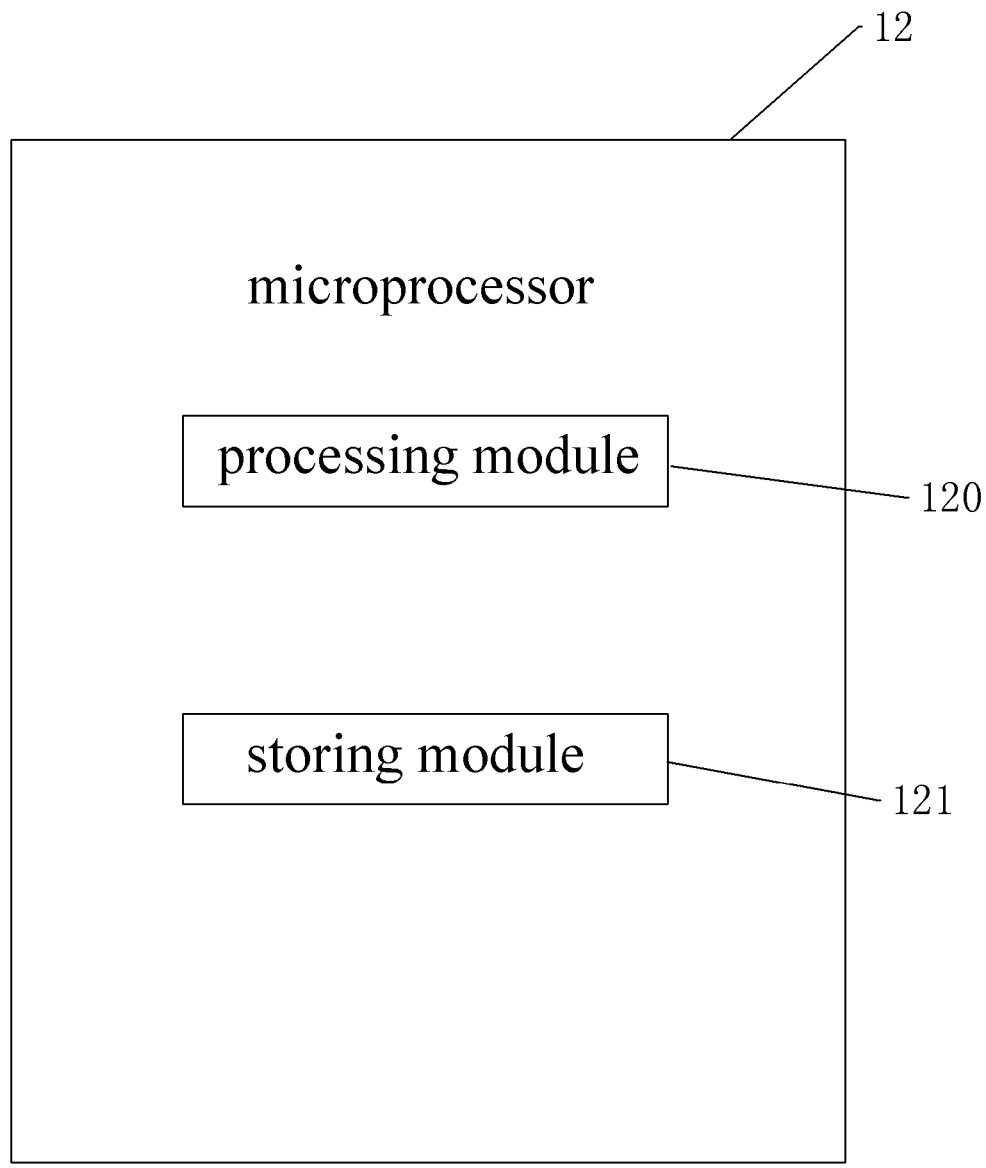
FIG. 3 is a functional block diagram of the microprocessor in FIG. 2.
Figure 4:
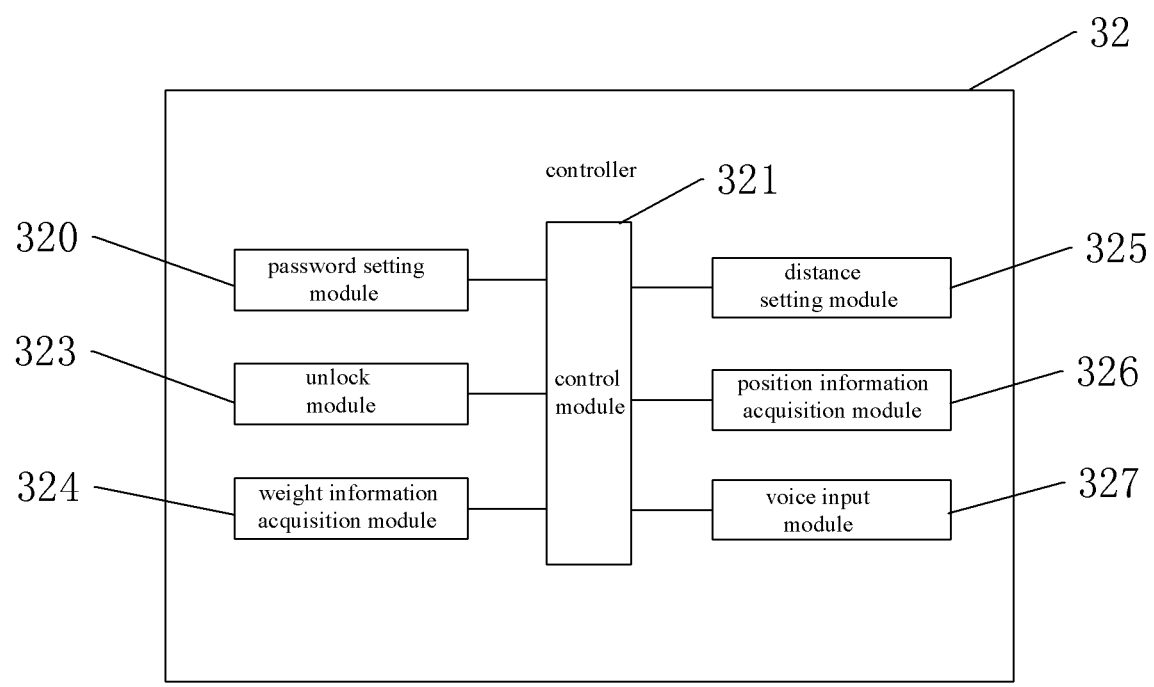
FIG. 4 is a functional block diagram of the controller in FIG. 2.

Specifically, see FIG. 3 and FIG. 4 of this embodiment. The controller 32 comprises password setting module 320 and control module 321 connected to the password setting module 320. The microprocessor 12 comprises a processing module 120 and a storing module 121 connected to said processing module 120. The password setting module 320 is displayed in the form of an identifier in the touch LCD screen 35. When consumers input unlocking password setting instruction and given unlocking password in the touch LCD screen 35, the password setting module 320 is used to generate unlocking password setting instruction and given unlocking password. The control module 321 receives the unlocking password setting instruction and given unlocking password, and controls the processing module 120 to store the given unlocking password in said storing module 121. It is to be explained that the password setting module 320 generating unlocking password setting instruction and given unlocking password means generating the digital information corresponding to unlocking password setting instruction and given unlocking password.

The specific principle of consumer's setting unlocking password is that: consumers firstly click the identifier representing the password setting module 320 in the touch LCD screen 35, and after the password setting module 320 is clicked, the unlocking password setting instruction will be generated. The control module 321, after receiving the unlocking password setting instruction, controls the password setting module 320 to be further displayed in the touch LCD screen 35 in the form of input interface, meanwhile the control module 321 sends the unlocking password setting instruction to the processing module 120. Consumers input given unlocking password from the input interface in the touch LCD screen 35. The password setting module 320 then generates the given unlocking password. The control module 321 receives the given the unlocking password and sends it to the processing module 120 that stores the given unlocking password in the storing module 121. It is understood that now the processing module 120 will overwrite the unlocking password previously stored in storing module 121.

In this embodiment, the controller 32 also comprises the unlocking module 323 connected to the control module 321. The unlocking module 323 is displayed in the form of identifier in the touch LCD screen 35. When consumers input unlocking instruction and unlocking password in the touch LCD screen 35, the unlocking module 323 generates the unlocking instruction and unlocking password. The control module 321 receives the unlocking instruction and unlocking password, and controls the processing module 120 to unlock the electronic combination lock 11. It is to be explained that the unlocking module 323 generating unlocking instruction and unlocking password means generating the digital information corresponding to the unlocking instruction and unlocking password.

The specific principle of consumer's unlocking electronic combination lock 11 is that: consumers first click the identifier representing the unlocking module 323 in the touch LCD screen 35; After the unlocking module 323 is clicked, the unlocking module 323 generates the unlocking instruction; The control module 321, after receiving the unlocking instruction, controls the unlocking module 323 to be further displayed in the touch LCD screen 35 in the form of input interface, meanwhile the control module 321 sends the unlocking instruction to the processing module 120. After consumers input unlocking password from the input interface in the touch LCD screen 35, the unlocking module 323 will further generate the unlocking password; the control module 321 will receive the unlocking password and send it to the processing module 120. The processing module 120 determines whether the received unlocking password is the same as the given unlocking password stored in the storing module 121, and when both are identical, the processing module will unlock the electronic combination lock 11. The controller 32 also comprises the weight information acquisition module 324 connected to the control module 321. The weight information of suitcase body 1 induced by the weight sensor 15 is stored in the storing module 121 by the processing module 120. The weight information acquisition module 324 is displayed in the form of an identifier in the touch LCD screen 35. When consumers input weight information instruction in the touch LCD screen 35, the weight information acquisition module 324 will generate the weight information acquisition instruction. The control module 321, when receiving the weight information acquisition instruction, displays the weight information stored in the storing module 121 in the touch LCD screen 35. The weight information acquisition module 324 generating weight information acquisition instruction means generating the digital information corresponding to the weight information acquisition instruction. It is understood that processing module 120, when storing weight information in the storing module 121, will overwrite the weight information previously stored in the storing module 121.

The specific principle of consumer's acquiring weight information of suitcase 1 is that: consumers first click the identifier representing weight information acquisition module 324 in the touch LCD screen 35; after the weight information acquisition module 324 is clicked, the weight information acquisition module 324 will generate the weight information acquisition instruction. The control module 321, after receiving weight information acquisition instruction, controls the weight information acquisition module 324 to be further displayed in the touch LCD screen 35 in the form of weight information display interface, meanwhile the control module 321 controls the processing module 120 to send back the weight information stored in the storing module 121, and the control module 321 will display the weight information in the touch LCD screen 35.

In this embodiment, the suitcase body 1 also comprises a radio-frequency signal transmitter 21 and an alarm 22 connected to the microprocessor 12, and the mobile control terminal 3 is also provided with a radio-frequency signal feedback device 36. The radio-frequency signal transmitter 21 is used to send electromagnetic wave signal, receive the feedback signal from the radio-frequency signal feedback device 36, and according to the feedback signal, calculate the actual distance between the radio-frequency signal transmitter 21 and the radio-frequency signal feedback device 36. The microprocessor 12 stores given anti-lost distance, and when it determines the actual distance is farther than given anti-lost distance, will start the alarm 22 to warn consumers that the suitcase body 1 is beyond the given anti-lost distance. Specifically, the storing module 121 of the microprocessor 12 stores the given anti-lost distance. The processing module 120 is used to receive actual distance and determine whether the actual distance is farther than the given anti-lost distance, and when it determines so, will start the alarm 22.

In this embodiment, the controller 32 also comprises a distance setting module 325 connected to the control module 321. The operating information input by consumers in the touch LCD screen 35 comprises anti-lost distance setting instruction and given anti-lost distance. When consumers input anti-lost distance setting instruction and given anti-lost distance by the touch LCD screen 35, the distance setting module 325 is used to generate anti-lost distance setting instruction and given anti-lost distance, and the control module 321 will receive the anti-lost distance setting instruction and given anti-lost distance and control the processing module 120 to store the given anti-lost distance in the storing module 121. It is to be explained that the distance setting module 325 generating anti-lost distance setting instruction and given anti-lost distance means generating the digital information corresponding to the anti-lost distance setting instruction and the given anti-lost distance.

The specific principle of consumer's setting anti-lost distance is that: consumers firstly click the identifier representing the distance setting module 325 in the touch LCD screen 35, and after the distance setting module 325 is clicked, the anti-lost distance setting instruction will be generated. The control module 321, after receiving the anti-lost distance setting instruction, controls the distance setting module 325 to be further displayed in the touch LCD screen 35 in the form of input interface, meanwhile the control module 321 sends the anti-lost distance setting instruction to the processing module 120. Consumers input given anti-lost distance from the input interface in the touch LCD screen 35, and then the distance setting module 325 will generate the given anti-lost distance. The control module 321 receives the given anti-lost distance and sends it to the processing module 120 that stores the given anti-lost distance in the storing module 121. It is understood that now the processing module 120 will overwrite the given anti-lost distance previously stored.

Furthermore, in this embodiment, the suitcase body 1 comprises a GPS positioner 16 connected to the microprocessor 12. When the microprocessor 12 determines the actual distance is farther than the given anti-lost distance, the microprocessor 12 will start the GPS positioner 16 and acquire the position information by GPS positioner 16, and send the position information of the suitcase body 1 to the controller 32. The position information will then be displayed in the touch LCD screen 35 by the controller 32, so that consumers can accurately know the position of suitcase. Specifically, the GPS positioner 16 is connected to the processing module 120, and the processing module 120 first stores the position information acquired by the GPS positioner 16 in the storing module 121. The controller 32 also comprises a position information acquisition module 326 connected to the control module 321, and the position information acquisition module 326 is displayed in the touch LCD screen 35. The operating information input by consumers from the touch LCD screen 35 comprises position information acquisition instruction, and the position information acquisition module 326 is used to generate the position information acquisition instruction. The control module 321, when receiving the position information acquisition instruction, controls the processing module 120 to display the position information stored in the storing module 121 in the touch LCD screen 35. It is to be noted that the position information acquisition module 326 generating the position information acquisition instruction means generating the digital information corresponding to the position information acquisition instruction. The processing module 120, when storing the position information in the storing module 121, will overwrite the position information previously stored in the storing module 121.

The principle of consumer's acquiring the position information of suitcase body 1 is that the following.

After consumers find their suitcase body 1 is lost, the consumers first click the identifier of position information acquisition module 326 in the touch LCD screen 35, and after the clicking of the identifier of position information acquisition module 326, a position information acquisition instruction will be generated. After the control module 321 receives the position information acquisition instruction and outputs a control signal to the processing module 120, the processing module 120 will send the position information stored in the storing module 121 to the control module 321, and then the control module 321 will display the position information sent from the processing module 120 in the touch LCD screen 35.

Specifically, in this embodiment, the suitcase body 1 comprises a power supply module 26 to provide power for the electric equipment in the suitcase body 1 such as the microprocessor 12, the radio-frequency signal transmitter 21, the GPS positioner 16, and wireless communication module. An electronic switch is disposed between the power supply module 26 and the GPS positioner 16, and the control end of the electronic switch is connected to the microprocessor 12. When the microprocessor 12 determines the actual distance is farther than the given anti-lost distance, the microprocessor 12 will turn off the electronic switch to allow the GPS positioner 16 to acquire the position information of the suitcase body 1 and send the position information of the suitcase body 1 to the microprocessor 12, thus saving the power. Of course in other embodiments, GPS positioner 16 can continuously acquire the position information of the suitcase body 1, namely, the position information of the suitcase body 1 is real-time sent to the mobile control terminal 3. When locating the position of the suitcase body 1, consumers may operate the position information of acquisition module 326 in the controller 32 to acquire the position information of the suitcase body 1.

It is to be noted that, in the above-mentioned embodiment, the first Bluetooth communication module 13 and the first remote wireless communication module 14 are all connected to the processing module 120, while the second Bluetooth communication module 33 and the second remote wireless communication module 34 are all connected to the control module 321. In normal connection between the first Bluetooth communication module 13 and the second Bluetooth communication module 33, the control module 321 and the processing module 120 transfer data via Bluetooth; If the connection between the first Bluetooth communication module 13 and the second Bluetooth communication module 33 is not available, two remote wireless communication modules are used for data transmission.

Figure 5:
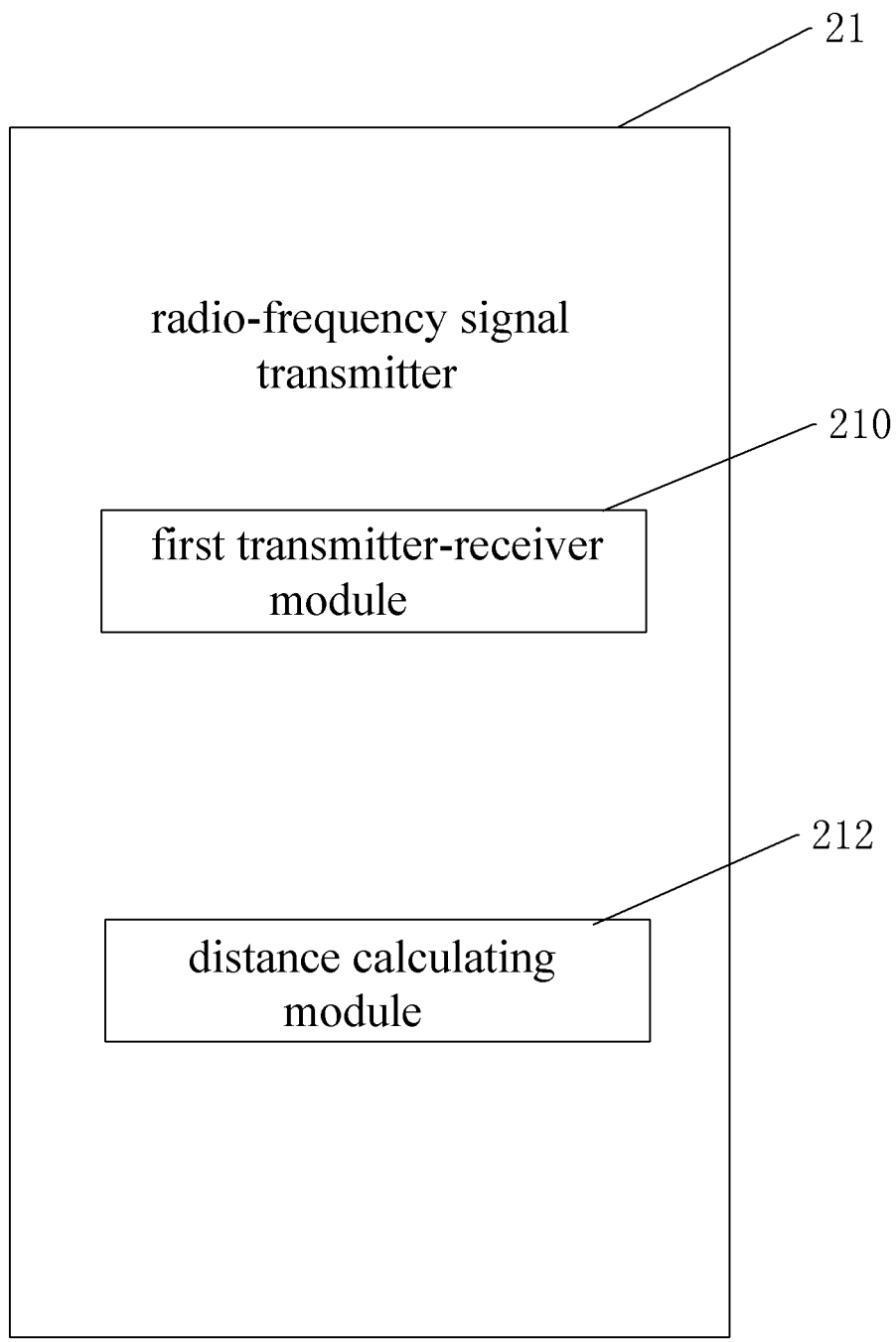
FIG. 5 is a functional block diagram of radio-frequency signal transmitter in FIG. 2.

See FIG. 5. The radio-frequency signal transmitter 21 comprises a first transmitter-receiver module 210 and a distance calculation module 212 connected to a first transmitter-receiver module 210. Said first transmitter-receiver module 210 is used to send electromagnetic wave signals to said radio-frequency signal feedback device 36 and receive the feedback signals from the radio-frequency signal feedback device 36; The distance calculation module 212 is used to, according to the feedback signals, calculate the actual distance between the radio-frequency signal transmitter 21 and the radio-frequency signal feedback device 36, and send the actual distance to said microprocessor 12. The specific principle of calculating actual distance by distance calculation module 212 is that: the radio-frequency signal transmitter 21 sends electromagnetic wave signal to the radio-frequency signal feedback device 36, and after receiving the signal, the radio-frequency signal feedback device 36 will send the feedback signal to the radio-frequency signal transmitter 21. The distance calculation module 212 will calculate the actual distance by the time difference between radio-frequency signal transmitter 21 sending electromagnetic wave signal and receiving feedback signal.

Figure 6:
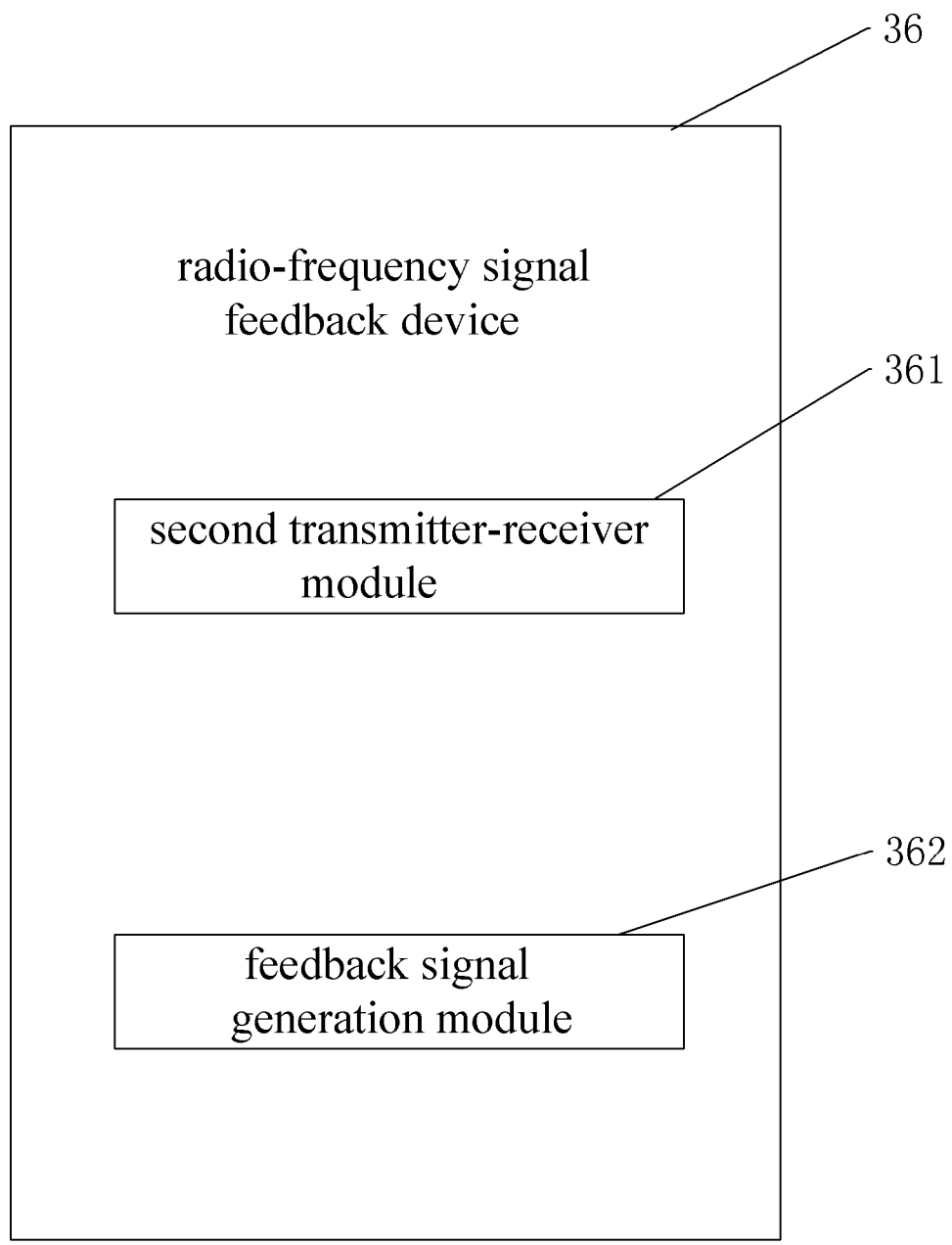
FIG. 6 is a functional block diagram of radio-frequency signal feedback device in FIG. 2.

See FIG. 6 in this embodiment. The radio-frequency signal feedback device 36 comprises a second transmitter-receiver module 361 and a feedback signal generation module 362 connected to the second transmitter-receiver module 361. Said second transmitter-receiver module 361 is used to receive the electromagnetic wave signals sent from said radio-frequency signal transmitter 21 and send the feedback signals to the radio-frequency signal transmitter 21; the feedback signal generation module 362 is used to generate feedback signal and send the feedback signal to the second transmitter-receiver module 361.

In this embodiment, both the first Bluetooth communication module 13 and the second Bluetooth communication module 33 use 4.0 Bluetooth-unit to guarantee transmitting signal in a mode of low power Bluetooth penetration between two Bluetooth communication modules.

In this embodiment, the first remote wireless communication module 14 and the second remote wireless communication module 34 are one of WIFI wireless communication module, zigbee communication module and GPRS communication module, so that the mobile control terminal 3 can realize the remote control over the suitcase body 1.

In this embodiment, the suitcase body 1 is provided with a drawbar 17 at its top and the roller wheels 18 in its bottom respectively, so that consumers can easily draw the suitcase body 1.

In this embodiment, the alarm 22 is a buzzer siren that can beep at alarm to warn suitcase owner.

In this embodiment, the suitcase body 1 also comprises an electronic switch 23, LED strip 24 and air quality monitoring module 25. The input end, control end and output end of the electronic switch 23 are respectively connected to the power supply module 26, the microprocessor 12 and LED strip 24. The air quality monitoring module 25 is used to collect current air quality information and sent it to the processing module 120 of the microprocessor 12. The storing module 121 of the microprocessor 12 stores the healthy air index. After receiving the current air quality information collected by the air quality monitoring module 25, the processing module 120 of the microprocessor 12 will determine whether the current air quality meets the healthy air index. If the current air quality does not meet the healthy air index, the processing module 120 will output control signal to turn on the electronic switch 23, so that the LED strip 24 will light up. The LED strip 24 is optionally provided outside the suitcase body 1 and around the suitcase body 1.

In this embodiment, the air quality monitoring module 25 optionally comprises PM2.5 sensor, fog sensor, carbon monoxide sensor, carbon dioxide sensor and formaldehyde sensor.

In this embodiment, the electronic switch 23 is a triode. The input end, output end and control end of the electronic switch 23 respectively correspond to the collector electrode, emitting electrode and base electrode of the triode, and the triode is arranged with high level conduction.

The mobile control terminal 3 also comprises a voice collector 327 connected to the controller 32. Consumers input audio acquisition instruction to the controller 32 through the touch LCD screen 35, and after receiving the audio acquisition instruction, the controller 32 will start the voice collector 327. The voice collector 327 is used to collect consumers' acoustical signal and send it to the control module 321 of the controller 32. The control module 321 of the controller 32 will then send the acoustical signal to the processing module 120 of the microprocessor 12, and control the processing module 120 of the microprocessor 12 to operate corresponding action.

Specifically, the controller 32 also comprises a voice input module 327 connected to the control module 321. The voice input module 327 is displayed in the form of identifier such as a voice input key in the touch LCD screen 35. Consumers are able to press the voice input key representing the voice input module to input voice collection instruction to the control module 321, and then the control module 321 will start the voice collector 327. The voice collector 327 collects consumers' acoustical signal and send it to the control module 321. The controller module 321 will send the acoustical signal to the processing module 120 of the microprocessor 12. The storing module 121 of the microprocessor 12 stores an acoustical signal model that optionally comprises a model representing the "displaying air quality" instruction. The processing module 120 of the microprocessor 12 then compares the received acoustical signal to the acoustical signal models. When the processing module 120 of the microprocessor 12 determines that the received acoustical signal matches the model representing the "displaying air quality" instruction, the processing module 120 of the microprocessor 12 will send the received air quality to the controller 32. The control module 321 of the controller 32 displays the air quality in the touch LCD screen 35, so that consumers can precisely know the air condition of current environment.

The suitcase body 1 also comprises a voice broadcasting device 28 connected to the microprocessor 12. The processing module 120 of the microprocessor 12 sent the current air quality to the voice broadcasting device 28; the voice broadcasting device 28 will then announce the current air quality received by the processing module 120 of the microprocessor 12. Specifically, the acoustical signal model optionally comprises the model representing "announcing air quality" instruction. When the processing module 120 of the microprocessor 12 determines that the received acoustical signal matches the model representing the "announcing air quality" instruction, the processing module 120 of the microprocessor 12 will send the received air quality to the voice broadcasting device 28, and the voice broadcasting device 28 will announce the current air quality received by the processing module 120 of the microprocessor 12, so that consumers can precisely know the air condition of current environment. It is to be explained that the working principle of voice broadcasting device 28 is a prior art and will not introduce it later.

The principle of the present invention's multifunctional intelligent suitcase that can detect air quality of ambient environment is the following.

The air quality monitoring module 25 collects the air quality of ambient environment at intervals according to the types of sensor such as PM2.5, fog, carbon monoxide, carbon dioxide, and formaldehyde, converts this information of PM2.5, fog, carbon monoxide, carbon dioxide, and formaldehyde into corresponding digits through A/D converter and sends them to the microprocessor 12. Then the microprocessor 12 determines whether the current air quality information collected by the air quality monitoring module 25 match the healthy air index. When either air quality of the current air quality does not meet the healthy air index, the microprocessor 12 will determine that the current air quality do not match healthy air index, and will then output a control signal (high level signal) to the electronic switch 23, thus the electronic switch 23 will be turned on and the LED strip 24 will light up, warning consumers that air quality does not meet the healthy air quality index.

Furthermore, consumers can operate corresponding actions controlled by the microprocessor 12 through the mobile control terminal 3. For example, when the LED strip lights up, consumers know the current ambient air quality does not meet the standard, but do not the concrete condition of current ambient air. Now consumers can operate the voice input key shown in the touch LCD screen 35 to start the voice collector 327 to collect operator's sound. For example, when consumers send the instruction of displaying current air quality on the touch LCD screen 35, the voice collector 327 will collect the voice information through an A/D converter and send it to the controller 32. The controller 32 will send the voice information to the microprocessor 12 for the comparison of the received acoustical signal to the acoustical signal models. When the microprocessor 12 determines that the received acoustical signal matches the model representing the "displaying air quality" instruction, the microprocessor 12 will send the received air quality to the controller 32, and the controller 32 will display the current air quality on the touch LCD screen 35, so that consumers can precisely know the air condition of current environment.

When the microprocessor 12 determines that the received acoustical signal matches the model representing the "announcing air quality" instruction, the microprocessor 12 will send the received air quality to the voice broadcasting device 28, and the voice broadcasting device 28 will announce the current air quality received by the microprocessor 12, so that consumers can precisely know the air condition of current environment.

The mobile control terminal 3 is optionally installed with an APP software, wherein the APP software has the functions of password setting, unlocking, weight information acquisition, distance setting and position information acquisition to enable the mobile control terminal 3 to have the functions of password setting, unlocking, weight information acquisition, distance setting, position information acquisition and voice input. That is to say, the password setting module 320, unlocking module 323, weight information acquisition module 324, distance setting module 325, position information acquisition module 326 and voice input module 327 of the controller 32 are optionally represented by specific identifiers displayed in the operating interface of the APP software. Consumers may first open the APP software and the operating interface is then displayed in the touch LCD screen 35. Consumers can input various operation information by clicking their specific identifiers in the touch LCD screen 35.

Figure 7:
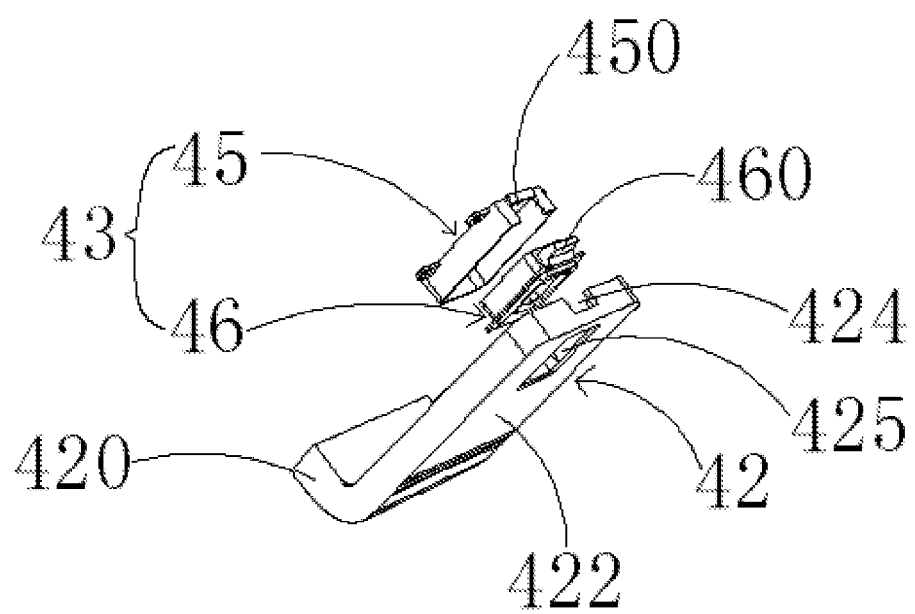
FIG. 7 is an exploded view of the clamshell and slide-snap module in FIG. 1.

Furthermore, see FIG. 1 and FIG. 7. The multifunctional intelligent suitcase comprises a battery compartment that consists of a one-side-openable compartment body 41, a clamshell 42 and a slide-snap module 43. The compartment body 41 is used to accept the batteries of power supply module 26 and mounted onto the casing of said suitcase body 1. In this embodiment, the compartment body 41 is mounted on the casing of said suitcase body 1. The upper casing is optionally provided with an opening, and the compartment body 41 penetrates the opening and is disposed in the suitcase body 1 with mounting blocks such as screws to fix it to the upper casing. One end of the clamshell 42 is hinged to the compartment body 41, and the other end of the clamshell 42 is provided with the securing module 43. When the clamshell 42 is recovered to the compartment body 41, the slide-snap module 43 is coupled to the buckle of the compartment body 41.

In this embodiment, said slide-snap module 43 comprises a slide cavity 45, a slide snap 46 and at least an elastic element (not shown in the drawing). The slide cavity 45 and the clamshell 42 are detachably mounted together optionally through screws. The slide snap 46 is disposed in the slide cavity 45, and both sides of the slide snap 46 touch the slide cavity 45 to slide along the slide cavity 45. The buckle 460 is at the top of the slide snap 46. The top of the compartment body 41 correspondingly has a buckle hole matching the buckle 460 (not shown in the drawing). The elastic element is provided between the bottom of the slide snap 46 and the slide cavity 45. When the clamshell 42 is pushed to cover the compartment body 41, the reversion strength of the elastic element promotes the slide snap 46 to move toward said buckle hole to enable the buckle 460 to match the buckle hole.

In this embodiment, the L-type clamshell 42 comprises a junction plate 420 and a covering plate 422 connected to the junction plate 420. The covering plate 422 is used to cover the compartment body 41. The junction plate 420 is provided with pivot shafts (not shown in the drawing) at both sides. The compartment body 41 is provided with corresponding pivotal holes (not shown in the drawing) to connect the pivot shafts and enable the clamshell 42 to hinge the compartment body 41.

In this embodiment, the slide cavity 45 is a one-side-openable square box and on its top provided with a first mouth 450 to allow the buckle 460 to penetrate it; the covering plate 422 is provided with a second mouth 424 on its top, and the slide cavity 45 is disposed behind the covering plate 422. The first mouth 450 and the second mouth 424 is aligned to combine a throughhole to allow the buckle 460 to penetrate it, so that the slide snap can slide along the slide cavity 45.

Furthermore, the covering plate 422 is provided with a cavity (not shown in the drawing) in the side facing the compartment body 41. The slide-snap module 43 is disposed in the cavity to avoid the covering plate 422 from interfering the slide of the slide snap 46.

Furthermore, in this embodiment, the covering plate 422 is provided with an operation mouth 425 across 422 both opposite faces of the covering plate 422. The slide-snap module 43 is installed behind the covering plate 422, and the operating mouth 425 is arranged opposite the slide snap 46 to facilitate pulling the slide snap 46.

Furthermore, the slide snap 46 is optionally provided with an operating groove in the face opposite to the operating mouth 425 to facilitate operating the slide snap 46.

The working principle of the present invention's detachable battery structure of the multifunctional intelligent suitcase is the following.

During security check at airport, if the batteries need to be removed from the suitcase, consumers can put out their finger into the operating mouth 425 and pulled down the slide snap 46 to force it to slide down along the slide cavity 45, so that the buckle 460 will detach the buckle hole. In such a way consumers can rotate the clamshell 42 and open the battery compartment to remove the batteries out of the compartment body 41. Then, consumers can recover the clamshell 42 to cover the compartment body 41. The buckle 460 of the slide snap 46 will contact the compartment body 41, and the buckle 460 will be pressed by the compartment body 41 to force the slide snap 46 to move downwards and press the elastic element. When the buckle 460 is aligned with the buckle hole, the elastic element will provide a force to the slide snap 46 to force the slide snap 46 to move upwards until the buckle 460 of the slide snap 46 clamps into the buckle hole, so that the slide-snap module 43 is coupled to the compartment body 41 to fix the clamshell 42 and the compartment body 41 together.

In this embodiment, the buckle 460 is in the form of wedge to facilitate the compartment body 41 to press the buckle 460.

In this embodiment, the elastic element is optionally a spring.

Furthermore, the multifunctional intelligent suitcase of the present invention also comprises a hub motor 27 to drive roller wheel. The hub motor 27 is connected to the microprocessor 12.

According to the feedback signal of the radio-frequency signal feedback device, the radio-frequency signal transmitter 21 can calculate the transmission route of the feedback signal, and send the calculated transmission route of the feedback signal to the microprocessor 12. The microprocessor 12 stores a given following distance. When it determines that the actual distance is farther than the given following distance, the microprocessor 12 will start the hub motor 27 and control it to drive the roller wheel 18 in accordance with the received transmission route of the feedback signal to enable the suitcase body 2 to move in the direction of radio-frequency signal feedback device 36, namely in the direction of suitcase owner, so that the automatic walking of the suitcase is realized. It is understood that the following distance is optionally stored in the storing module 121 of the microprocessor 12, and the action of the hub motor 27 is controlled by the processing module 120 of the microprocessor 12. The distance calculating module 212, according to the received feedback signal, calculates the transmission route of the feedback signal and optionally the method of calculating the transmission route of the feedback signal in missile tracing technology can be adopted.

The multifunctional intelligent suitcase of the present invention has the facilitating functions of remote unlocking, remote password setting, air quality monitor, battery loading and unloading, and automatic tracing.

The description of above-mentioned embodiment is only to help understand the method and core thought of the present invention. It will be obvious to those skilled in the art that variations, supplementation or replacement with similar mode may be made in the construction and relation of parts without departing from the spirit and scope of the invention described herein, and fall within the basic claims herein set forth.

The above description of published embodiments enables the persons skilled in the art can realize or use the present invention. Various changes to these embodiments may be evident to those skilled in the art. The general theory specified by the present invention may be realized in other examples without departing from the spirit and scope of the present invention. Hence, the present invention shall not be limited to the embodiment shown in this paper but conform to the widest range of principles and novel features that are disclosed in this paper.

What is claimed is:

1. A multifunctional intelligent suitcase, comprising: a suitcase body and a mobile control terminal; said suitcase body is provided with an electronic combination lock, a microprocessor, a first Bluetooth communication module, a first remote wireless communication module, an electronic switch, a power supply module, an LED strip and an air quality monitoring module; said electronic combination lock, said first Bluetooth communication module and said first remote wireless communication module are all connected to said microprocessor; said mobile control terminal comprises a controller, a second Bluetooth communication module, a second remote wireless communication module and a touch LCD screen; said second Bluetooth communication module, said second remote wireless communication module and said touch LCD screen are all connected to said controller; said second Bluetooth communication module is one-to-one wirelessly connected with said first Bluetooth communication module; said first remote wireless communication module is one-to-one wirelessly connected with said second remote wireless communication module; in the connection between said first Bluetooth communication module and said second Bluetooth communication module, said microprocessor and said controller realize mutual data transmission via Bluetooth communication; said touch LCD screen is used for consumers to input operating information; said operating information comprises unlocking setting instruction, given unlocking password, unlocking instruction and unlocking password; said controller is used to control said microprocessor to set or unlock said electronic combination lock in accordance with said operation information; the input end, control end and output end of said electronic switch are respectively connected to said power supply module, said microprocessor and said LED strip; said air quality monitoring module is connected to said microprocessor to collect the information of current air quality and transmit the information collected to said microprocessor; said microprocessor stores the data of healthy air for comparison and judgment; when it determines information of the current air quality fails to meet the data of healthy air, said microprocessor will output a signal to turn on said electronic switch and enable said LED strip to light up.

2. The multifunctional intelligent suitcase according to claim 1, wherein said controller comprises password setting module and a control module connected to said password setting module; said microprocessor comprises a processing module and a storing module connected to said processing module; said password setting module is used to generate said unlocking setting instruction and given unlocking password; and said control module receives said unlocking setting instruction and given unlocking password, and controls said processing module to store said given unlocking password in said storing module.

3. The multifunctional intelligent suitcase according to claim 2, wherein said controller comprises an unlocking module connected to said control module; said unlocking module is used to generate said unlocking instruction and said unlocking password; said control module receives said unlocking instruction and said unlocking password, and transmits said unlocking instruction and said unlocking password to said processing module; said processing module determines whether said unlocking password matches the given unlocking password stored in said storing module, and when both match each other, said processing module unlocks the electronic combination lock.

4. The multifunctional intelligent suitcase according to claim 1, wherein said mobile control terminal comprises a voice collector connected to said controller; the touch LCD screen is used for consumers to input audio acquisition instruction to said controller and after receiving said audio acquisition instruction, said controller will start said voice collector; said voice collector is used to collect consumers' audio signals and transmit said audio signals to said controller; said controller transmits said audio signals to said microprocessor.

5. The multifunctional intelligent suitcase according to claim 1, wherein said multifunctional intelligent suitcase comprises a battery compartment that consists of a one-side-openable compartment body, a clamshell and a slide-snap module; said compartment body is used to accept the batteries of power supply module and mount onto the upper case body of said suitcase; one end of said clamshell is hinged to said compartment body, and the other end of said clamshell is provided with said securing module, when said clamshell is recovered to said compartment body, said slide-snap module is coupled to the buckle of said compartment body.

6. The multifunctional intelligent suitcase according to claim 5, wherein said slide-snap module comprises slide cavity, slide snap and at least an elastic element; said slide cavity is detachably mounted onto said clamshell; said slide snap locates inside said slide cavity and slides along the slide cavity; said slide snap is provided in its top with a buckle, and said compartment body is provided in its top with a buckle hole to match the buckle; said elastic element is provided between the bottom of said slide snap and said slide cavity; when said clamshell is pushed to cover said compartment body, the reversion strength of said elastic element promotes said slide snap to move in the direction of said buckle hole.

7. The multifunctional intelligent suitcase according to claim 6, wherein a covering plate is provided with an operation mouth across both opposite faces of the covering plate; said slide-snap module is disposed behind said covering plate, and said operation mouth is arranged opposite said slide snap.

8. The multifunctional intelligent suitcase according to claim 1, wherein said suitcase body is provided with roller wheels in its bottom; said suitcase body is also arranged inside its body with a hub motor to drive said roller wheels and radio-frequency signal transmitter; both said hub motor and said radio-frequency signal transmitter are connected to said microprocessor; said mobile control terminal comprises a radio-frequency signal feedback device; said radio-frequency signal transmitter and said radio-frequency signal feedback device are wireless connected for the calculation of the actual distance between the radio-frequency signal transmitter and the radio-frequency signal feedback device; said microprocessor stores a given following distance, and receives said actual distance to determine whether said actual distance is farther than said following distance, and when said actual distance is farther than said following distance, said microprocessor will start said hub motor.

9. The multifunctional intelligent suitcase according to claim 8, wherein said radio-frequency signal transmitter comprises a first transmitter-receiver module and a distance calculation module connected to said first transmitter-receiver module; said first transmitter-receiver module is used to send electromagnetic wave signals to said radio-frequency signal feedback device and receive the feedback signals from said radio-frequency signal feedback device; said distance calculation module is used to, according to the feedback signals, calculate the actual distance between said radio-frequency signal transmitter and said radio-frequency signal feedback device, and send the actual distance to said microprocessor.

10. The multifunctional intelligent suitcase according to claim 9, wherein said radio-frequency signal feedback device comprises a second transmitter-receiver module and a feedback signal generation module connected to said second transmitter-receiver module; said second transmitter-receiver module is used to receive the electromagnetic wave signals sent from said radio-frequency signal transmitter and send the feedback signals to said radio-frequency signal transmitter; said feedback signal generation module is used to generate feedback signals.

\* \* \* \* \*